United States Patent [19]

Pearson et al.

[11] Patent Number: 5,190,574

[45] Date of Patent: Mar. 2, 1993

[54] HERBICIDAL PYRAZOLYLOXY AND PYRAZOLYLAMINO-BENZOTRIAZOLES

[75] Inventors: David P. J. Pearson, Maidenhead; John E. D. Barton, Reading; Christopher J. Mathews, Maidenhead; David Cartwright, Reading; Susan P. Barnett, Bracknell, all of England

[73] Assignee: Imperial Chemical Industries plc, London, England

[21] Appl. No.: 653,206

[22] Filed: Feb. 7, 1991

[30] Foreign Application Priority Data

Feb. 16, 1990 [GB] United Kingdom ............... 9003556
Sep. 5, 1990 [GB] United Kingdom ............... 9019345

[51] Int. Cl.$^5$ ............... A01N 43/647; C07D 401/12; C07D 401/14
[52] U.S. Cl. ............... 504/225; 548/257; 548/259; 548/260; 548/261; 544/129; 544/132; 546/187; 546/199; 504/248; 504/249; 504/282; 504/180; 504/181; 504/177
[58] Field of Search ............... 71/92, 88; 548/257, 548/259, 260, 261; 544/129, 132; 546/187, 199

[56] References Cited

FOREIGN PATENT DOCUMENTS 178708 4/1986 European Pat. Off. .
295233 6/1988 European Pat. Off. .
299446 1/1989 European Pat. Off. .
2157679 10/1985 United Kingdom .

Primary Examiner—Patricia L. Morris
Attorney, Agent, or Firm—Joel G. Ackerman

[57] ABSTRACT

A herbicidal compound of formula (I):

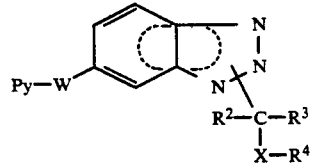

(I)

in which
the dotted line indicates the presence of two double bonds arranged so as to form a fused hetero-aromatic ring system;
Py is an optionally substituted pyrazole ring;
W is O or $NR^1$; where $R^1$ is hydrogen or lower alkyl;
X is $(CH_2)_n$, $CH=CH$, $CH(OR^5)CH_2$, $COCH_2$;
where n is 0, 1 or 2;
$R^2$ and $R^3$ are independently selected from H, optionally substituted alkyl, alkenyl or alkynyl, halogen, $NR^6R^7$, or $R^2$ and $R^3$ together with the carbon to which they are attached form an optionally substituted alkenyl or cycloalkyl group;
$R^4$ is $CO_2R^8$, CN, $COR^8$, $CH_2OR^8$, $CH(OH)R^8$, $CH(OR^8)R^9$, $CSNH_2$, $COSR^8$, $CSOR^8$, $CONHSO_2R^8$, $CONR^{10}R^{11}$, $CONHNR^{10}R^{11}$, $CONHN+R^{10}R^{11}R^{12}R^{14-}$, $CO_2{}^-R^{15+}$ or $COON=CR^{10}R^{11}$;
$R^{15+}$ is an agriculturally acceptable cation and $R^{14-}$ is an agriculturally acceptable anion.
$R^5$, $R^8$ and $R^9$ are independently selected from H or an optionally substituted alkyl, aryl, alkenyl or alkynyl group;
$R^6$, $R^7$, $R^{10}$, $R^{11}$ and $R^{12}$ are independently selected from H or an optionally substituted alkyl, alkenyl, aryl or alkynyl group; or any two of $R^6$, $R^7$, $R^{10}$, $R^{11}$ and $R^{12}$ together with the atom to which they are attached form a cycloalkyl or heterocyclic ring.

Processes for the preparation of these compounds and compositions containing them are also described.

11 Claims, No Drawings

HERBICIDAL PYRAZOLYLOXY AND PYRAZOLYLAMINO-BENZOTRIAZOLES

The present invention relates to novel substituted benzotriazole derivatives, processes for their preparation, their use as herbicides and herbicidal compositions containing them.

European Patent No. 178,708 A describes certain benzheterocyclyl-phenyl ether derivatives which have herbicidal activity.

According to the present invention there is provided a compound of formula (I):

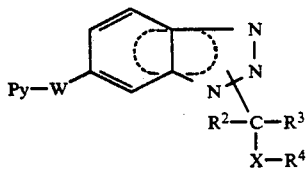

in which
the dotted line indicates the presence of two double bonds arranged so as to form a fused hetero-aromatic ring system;
Py is an optionally substituted pyrazole ring;
W is O or $NR^1$; where $R^1$ is hydrogen or lower alkyl;
X is $(CH_2)_n$, $CH=CH$, $CH(OR_5)CH_2$, $COCH_2$;
where n is 0, 1 or 2;
$R^2$ and $R^3$ are independently selected from H, optionally substituted alkyl, alkenyl or alkynyl, halogen, $NR^6R^7$, or $R^2$ and $R^3$ together with the carbon to which they are attached form an optionally substituted alkenyl or cycloalkyl group;
$R^4$ is $CO_2R^8$, CN, $COR^8$, $CH_2OR^8$, $CH(OH)R^8$, $CH(OR^8)R^9$, $CSNH_2$, $COSR^8$, $CSOR^8$, $CONHSO_2R^8$, $CONR^{10}R^{11}$, $CONHNR^{10}R^{11}$, $CONHN^+R^{10}R^{11}R^{12}R^{14-}$, $CO_2-R^{15+}$ or $COON=CR^{10}R^{11}$;
$R^{15+}$ is an agriculturally acceptable cation and $R^{14-}$ is an agriculturally acceptable anion.
$R^5$, $R^8$ and $R^9$ are independently selected from H or an optionally substituted alkyl, aryl, alkenyl or alkynyl group;
$R^6$, $R^7$, $R^{10}$, $R^{11}$ and $R^{12}$, are independently selected from H or an optionally substituted alkyl, alkenyl, aryl or alkynyl group; or any two of $R^6$, $R^7$, $R^{10}$, $R^{11}$ and $R^{12}$ together with the atom to which they are attached form a cycloalkyl or heterocyclic ring.

As used herein the term "alkyl" includes straight or branched chains containing up to 10 carbon atoms preferably from 1 to 6 carbon atoms. The terms "alkenyl" and "alkynyl" refer to unsaturated straight or branched chains having from 2 to 10 and preferably from 2 to 6 carbon atoms. The term "cycloalkyl" includes rings containing from 3 to 9 carbon atoms, preferably from 3 to 6 carbon atoms. The term "alkoxy" includes straight or branched chains containing up to 10 carbon atoms preferably from 1 to 6 carbon atoms. The term "lower" used in relation to alkyl, alkenyl or alkynyl groups means that the group contains up to 3 carbon atoms.

The term "haloalkyl" and "haloalkoxy" refer to alkyl and alkoxy groups respectively substituted by at least one halogen atom such as fluorine, chlorine or bromine. A particular haloalkyl group is trifluoromethyl. The term "heterocyclic" includes rings of up to 10 atoms, preferably up to 6 atoms up to 3 of which are selected from oxygen, nitrogen or sulphur. The term halogen includes fluorine, chlorine, bromine and iodine.

Suitable optional substituents for the group Py include up to 3 groups selected from halogen (such as fluoro, chloro, bromo or iodo); a group $R^x$ where $R^x$ is a group as defined hereinbefore for nitro; haloalkoxy (such as $OCF_3$); a group $S(O)_mR^y$ where m is 0, 1 or 2 and $R^y$ is a group as hereinbefore defined for $R^8$; or $R^z$ where $R^z$ is a group as hereinbefore defined for $R^4$.

Suitable optionally-substituted pyrazole ring systems Py are those of sub-formula (i):

where
$R^{16}$ is halogen, CN, haloalkyl, optionally substituted alkyl, $S(O)_m R^y$ where m and $R^y$ are as hereinbefore defined;
$R^{17}$ is H, halogen, CN, alkyl, haloalkyl, a group $S(O)_mR^y$ where m and $R^y$ are as hereinbefore defined, nitro or a group $R^z$ as hereinbefore defined; and
$R^{18}$ is optionally substituted alkyl, alkenyl or alkynyl.
Preferably $R^{16}$ is haloalkyl, in particular $CF_3$.
$R^{17}$ is preferably H, halogen, CN, alkyl, haloalkyl or nitro. In particular $R^{17}$ is hydrogen, halogen, especially chloro or methyl.
$R^{18}$ is preferably $C_{1-6}$ alkyl, in particular methyl.

Suitable optional substitutents for the aryl groups $R^5$, $R^6$, $R^7$, $R^8$, $R^9$, $R^{10}$, $R^{11}$, $R^{12}$ and $R^{13}$ are up to 5 preferably up to 3 members selected from halogen (fluoro, chloro, bromo or iodo), lower alkyl, haloalkyl (for example $CF_3$), haloalkoxy (for example $OCF_3$), nitro, cyano, lower alkoxy (for example methoxy) or $S(O)_qR^w$ where q is 0, 1 or 2 and $R^w$ is alkyl (for example thiomethyl, sulphinylmethyl and sulphonylmethyl).

Examples of optional substituents for alkyl, alkenyl, alkynyl groups $R^2$, $R^3$, $R^5$, $R^6$, $R^7$, $R^8$, $R^9$, $R^{10}$, $R^{11}$ and $R^{12}$ include one or more groups selected from halo such as fluoro, chloro or bromo; nitro; cyano; aryl such as phenyl; $CO_2R^{19}$, $NHCOR^{19}$ or $NHCH_2CO_2R^{19}$ wherein $R^{19}$ is hydrogen, $C_{1-6}$ alkyl or an agriculturally acceptable cation; $C_{1-6}$ alkoxy; oxo; $S(O)_NR^w$ where q and $R^w$ are as defined above (for example thiomethyl, sulphinylmethyl and sulphonylmethyl); amino; mono- or di- $C_{1-6}$ alkylamino; $CONR^{20}R^{21}$ wherein $R^{20}$ and $R^{21}$ are independently selected from hydrogen, $C_{1-6}$ alkyl, $C_{2-6}$ alkenyl or $C_{2-6}$ alkynyl or $R^{20}$ and $R^{21}$ are joined together to form a heterocyclic ring having up to 7 ring atoms 3 of which may be selected from oxygen, nitrogen or sulphur. An example of a heterocyclic substitutent is tetrahydrofuranyl.

Examples of agriculturally acceptable cations $R^{15+}$ or $R^{19}$ include sodium, potassium or calcium ions, sulphonium or sulphoxonium ions for example of formula $S(O)_fR^{10}R^{11}R^{12}$ where f is 0 or 1 or ammonium or tertiary ammonium ions of formula $N^+R^{10}R^{11}R^{12}R^{13}$ where $R^{10}$, $R^{11}$ and $R^{12}$ are as hereinbefore defined and $R^{13}$ is a further group as defined for $R^{10}$. Suitable substituents for alkyl, alkenyl and alkynyl groups in these cations include hydroxy and phenyl. Suitably where any of $R^{10}$, $R^{11}$, $R^{12}$ and $R^{13}$ are optionally substituted alkyl, they contain from 1 to 4 carbon atoms.

Particular examples of $R^{10}$, $R^{11}$, $R^{12}$ and $R^{13}$, in these cations are hydrogen, ethyl, isopropyl 2-hydroxyethyl and benzyl.

Examples of agriculturally acceptable anions $R^{14-}$ include halide such as iodide.

Suitable halo groups $R^2$ and $R^3$ include fluorine, chlorine and bromine.

Suitable heterocyclic rings formed from two of $R^6$, $R^7$, $R^{10}$, $R^{11}$ and the atom to which they are attached are pyrrolidine, piperidine and morpholine.

Preferably $R^2$ is H.

Preferably $R^3$ is H or is $C_{1-3}$ alkyl, in particular methyl.

Preferably $R^4$ is $CO_2R^8$ or $CO_2-R^{15+}$.

A preferred example of $R^8$ is $C_{1-6}$ alkyl, especially ethyl.

W is preferably oxygen.

Preferably X is $(CH_2)_n$ where n is zero or 1, especially zero.

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Some of the compounds of the invention can exist in enantiomeric forms. The invention includes both individual enantiomers and mixtures of the two in all proportions.

Particular examples of compounds according to the invention are listed in Tables I, II and III.

TABLE I

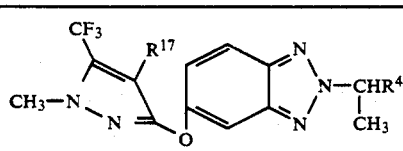

| Compound No. | $R^{17}$ | $R^4$ | Characterising Data |
|---|---|---|---|
| 1 | Cl | $CO_2C_2H_5$ | NMR(CDCl$_3$): 1.25(t)3H; 2.05(d)3H; 3.9(s)3H; 4.2(q)2H; 5.64(q)1H; 7.4(dd)1H; 7.5(d)1H; 7.85(d)1H. |
| 2 | H | $CO_2C_2H_5$ | NMR(CDCl$_3$): 1.2(t)3H; 2.0(d)3H; 3.9(s)3H; 4.2(q)2H; 5.65(q)1H; 6.2(s)1H; 7.3(dd)1H; 7.5(d)1H; 7.9(d)1H. |
| 3 | H | $CO_2H$ | m.p. 137°(dec.) NMR(DMSO): 1.95(d)3H; 4.0(s)3H; 5.45(q)1H; 6.7(s)1H; 7.4(dd)1H; 7.7(d)1H; 8.1(d)1H. |

TABLE II

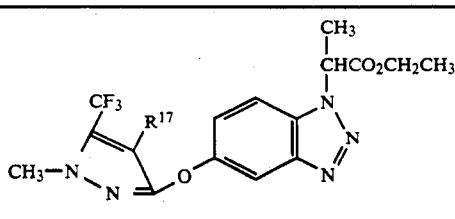

| Compound No. | $R^{17}$ |
|---|---|
| 4 | Cl |
| 5 | H |

TABLE III

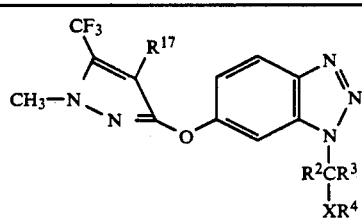

| Compound No. | $R^{17}$ | $CR^2R^3XR^4$ | Characterising Data |
|---|---|---|---|
| 6 | Cl | HC—$CO_2C_2H_5$ <br> \| <br> $CH_3$ | NMR(CDCl$_3$): 1.2(t)3H; 2.0(d)3H; 3.9(s)3H; 4.2(q)2H; 5.6(q)1H; 7.2(m)2H; 8.0(d)1H. |
| 7 | H | HC—$CO_2C_2H_5$ <br> \| <br> $CH_3$ | NMR(CDCl$_3$), 1.2(t)3H, 2.0(d)3H; 3.9(s)3H; 4.2(q)2H; 5.6(q)1H; 6.2(s)1H; 7.2(m)2H; 8.05(d)1H. |
| 8 | H | HC—$CH_2OH$ <br> \| <br> $CH_3$ | m.p. 104-106° NMR(CDCl$_3$): 1.65(d)3H; 3.1(t)1H; 3.9(s)3H; 4.1(m)1H; 4.25(m)1H; 4.85(m)1H; 6.2(d)1H; 7.1(dd)1H; 7.3(d)1H; 7.85(d)1H. |
| 9 | Cl | HC—$CH_2OH$ <br> \| <br> $CH_3$ | m.p. 153-154° NMR(CDCl$_3$): 1.65(d)3H; 3.1(m)1H; 3.9(s)3H; 4.1(m)1H; 4.25(m)1H; 4.85(m)1H; 7.1(dd)1H; 7.25(d)1H; 7.85(d)1H. |
| 10 | H | HC—$CO_2H$ <br> \| <br> $CH_3$ | m.p. 169-171° NMR(DMSO): 2.0(d)3H; 4.0(s)3H; 6.0(q)1H; 6.8(s)1H; 7.4(dd)1H; 7.7 (d)1H; 8.2(d)1H; 13.6(b)1H. |
| 11 | Cl | HC—$CO_2H$ <br> \| <br> $CH_3$ | m.p. 209-211° NMR(DMSO): 2.0(d)3H; 4.05(s)3H; 6.05(q)1H; 7.4(dd)1H; 7.7(d)1H; 8.2(d)1H. |
| 12 | Cl | HC—$CO_2CH_3$ <br> \| <br> $CH_3$ | NMR(CDCl$_3$): 2.0(d)3H; 3.7(s)3H; 3.9(s)3H; 5.6(q)1H; 7.2(m)2H; 8.05(d)1H. |

TABLE III-continued

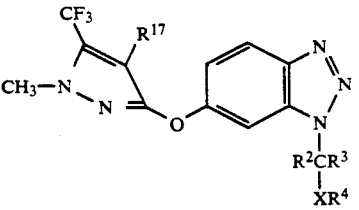

| Compound No. | R17 | CR2R3XR4 | Characterising Data |
|---|---|---|---|
| 13 | Cl | HC—CO2CH(CH3)2, CH3 | NMR(CDCl3) 1.15(m)6H; 2.0(d)3H; 3.9(s)3H; 5.05(m)1H; 5.55(q)1H; 7.2(m)2H; 8.05(d)1H. |
| 14 | Cl | HC—CO2(CH2)3CH3, CH3 | NHR(CDCl3): 0.8(t)3H; 1.2(m)2H; 1.5(m)2H; 2.0(d)3H; 3.9(s)3H; 4.1(t)2H; 5.6(q)1H; 7.2(m)2H; 8.0(d)1H. |
| 15 | Cl | HC—CONHCH3, CH3 | m.p. 190–192° NMR(CDCl3): 2.0(d)3H; 2.7(d)3H; 3.95(s)3H; 5.4(q)1H; 6.2(b)1H; 7.25(m)2H; 8.0(d)1H. |
| 16 | Cl | HC—CONH2, CH3 | m.p. 200–201° NMR(DMSO): 2.0(d)3H; 4.05(s)3H; 5.8(q)1H; 7.35(dd)1H; 7.6(b)1H; 7.7(d)1H; 7.8(b)1H; 8.2(d)1H. |
| 17 | Cl | (CH2)2OH | m.p. 126–128° C. NMR(CDCl3): 3.9(s)3H; 4.2(m)2H; 4.65(m)2H; 7.1(dd)1H; 7.25(d)1H; 7.8(d)1H. |
| 18 | Cl | HC—CN, CH3 | m.p. 147–150° C. NMR(CDCl3): 2.1(d)3H; 3.9(s)3H; 5.9(q)1H; 7.3(dd)1H; 7.45(d)1H; 8.1(d)1H. |
| 19 | Br | HC—CH2OH, CH3 | m.p. 142–144° C. NMR(CDCl3): 1.65(d)3H; 3.95(s)3H; 4.2(m)2H; 4.85(m)1H; 7.1(dd)1H; 7.25(d)1H; 7.9(d)1H. |
| 20 | Br | HC—CO2H, CH3 | m.p. 208–210° C. NMR(DMSO): 1.8(d)3H; 3.9(s)3H; 5.85(m)1H; 7.15(dd)1H; 7.5(d)1H; 8.05(d)1H; 13.4(s)1H. |
| 21 | Br | HC—CO2CH3, CH3 | NMR(CDCl3): 2.0(d)3H; 3.7(s)3H; 3.95(s)3H; 5.6(q)1H; 7.2(m)2H; 8.05(d)1H. |
| 22 | Br | HC—CO2CH2CH3, CH3 | NMR(CDCl3): 1.2(t)3H; 2.0(d)3H; 3.95(s)3H; 4.2(q)2H; 5.6(q)1H; 7.2(m)2H; 8.05(d)1H. |

TABLE III-continued

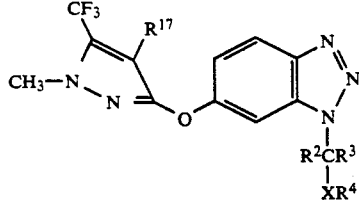

| Compound No. | R17 | CR2R3XR4 | Characterising Data |
|---|---|---|---|
| 23 | CH3 | HC—CH2OH, CH3 | m.p. 114–117° C. NMR(CDCl3): 1.6(d)3H; 2.0(m)3H; 3.0(b)1H; 3.9(s)3H; 4.2(m)2H; 4.8(m)1H; 7.1(m)2H; 7.9(d)1H. |
| 24 | CH3 | HC—CO2H, CH3 | m.p. 197–199° C. NMR(DMSO): 1.8(d)3H; 1.9(d)3H; 3.8(s)3H; 5.85(q)1H; 7.1(dd)1H; 7.4(d)1H; 8.0(d)1H. |
| 25 | CH3 | HC—CO2CH3, CH3 | m.p. 68–70° C. NMR(CDCl3): 2.0(m)6H; 3.7(s)3H; 3.9(s)3H; 5.6(q)1H; 7.15(m)2H; 8.0(d)1H. |
| 26 | CH3 | HC—CO2C2H5, CH3 | m.p. 60–62° C. NMR(CDCl3): 1.2(t)3H; 2.0(m)6H; 3.9(s)3H; 4.2)q)2H; 5.55(q)1H; 7.1(m)2H; 8.0(d)1H. |
| 27 | CH3 | HC—CO2(CH2)3CH3, CH3 | NMR(CDCl3); 0.8(t)3H; 1.2(m)2H; 1.5(m)2H; 2.0(m)6H; 3.9(s)3H; 4.1(t)2H; 5.55(q)1H; 7.15(m)2H; 8.0(d)1H. |
| 28 | CH3 | HC—CO2−Na+, CH3 | m.p. 235–237° C. NMR(D2O); 1.8(m)6H; 3.8(s)3H; 5.25(q)1H; 7.0(s)1H; 7.15(d)1H; 7.9(d)1H. |

Compounds of formula (I) may be prepared by reacting a compound of formula (II):

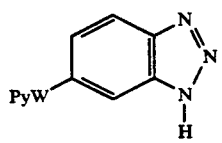
(II)

wherein Py and W are as defined in relation to formula (I) with a compound of formula (III):

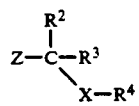
(III)

wherein X, $R^2$, $R^3$ and $R^4$ are as defined in relation to formula (I) and Z is a leaving group, optionally in the presence of a base.

Suitable leaving groups Z include halogen, such as fluorine, bromine and chlorine, and sulphonates such as methanesulphonate and p-toluenesulphonate.

Suitable bases for use in the reaction include bases such as sodium hydride, and alkali metal carbonates and hydroxides, or alkoxides.

The reaction is preferably carried out in an organic solvent such as dimethylformamide, dimethylsulphoxide, acetonitrile, tetrahydrofuran, a lower alkanol, or a lower alkyl ketone. Moderate temperatures, for example of from 20° to 90° C. are suitably employed. Conveniently the reaction is carried out at 25° to 30° C.

Compounds of formula (II) can be prepared from compounds of formula (IV):

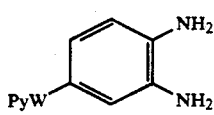
(IV)

wherein Py and W are as defined in relation to formula (I) except that W is not NH, by diazotisation for example with nitrous acid in a suitable solvent such as aqueous acetic acid or aqueous hydrochloric aid e.g. according to Campbell et al., J Chem Soc,1969,742.

Compounds of formula (IV) are prepared by reduction of the corresponding nitro compound of formula (V):

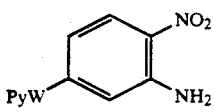
(V)

where Py and W are as defined in relation to formula (I).

A wide variety of reducing agents may be used and may be selected from the chemical literature by the skilled worker in the art. The reduction may be carried out for example by using sodium dithionite or tin and hydrochloric acid, iron and hydrochloric acid, or either hydrogen or a suitable hydrogen donor such as sodium borohydride with a palladium on charcoal catalyst. The reaction is effected in an organic solvent such as a lower alkyl alcohol optionally mixed with water at temperatures of from 20° C. to 90° C.

Compounds of formula (V) can be prepared from compounds of formula (VI):

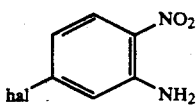
(VI)

in which hal is fluorine, chlorine, bromine or iodine by reaction with compounds of formula (VII):

 Py—WH (VII)

wherein Py and W are as defined in relation to formula (I). This reaction is carried out using a suitable base such as sodium hydride, alkali metal carbonates and hydroxides or alkoxides. The reaction is preferably carried out in an organic solvent such as dimethylformamide, dimethylsulphoxide, acetonitrile, tetrahydrofuran, a lower alkanol or a ketone. Moderate temperatures, for example of from 15°-90° C. are suitably employed.

Another method for preparing compounds of formula (IV) is shown in the following scheme where $R^{22}$ is lower alkyl, $R^{23}$ is halogen e.g. fluorine and Py is as defined in relation to formula (I):

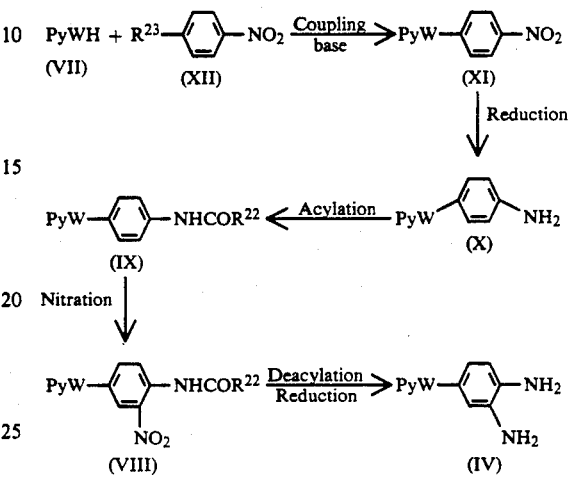

Compounds of formula (III), (VI) and (VII) are known compounds or they can be prepared from known compounds by known methods.

These processes will produce a mixture of 3 isomers in which the group $CR^2R^3XR^4$ is attached to the benzotriazole ring at the 1, 2 or 3 positions. In suitable cases the isomers may be separated by conventional procedures e.g. flash chromatography.

An alternative method of preparing compounds of formula (I) which will yield only one isomer where the group $CR^2R^3XR^4$ is attached at the 1 position of the benzotriazole ring consists of the diazotisation of compounds of formula (XIII):

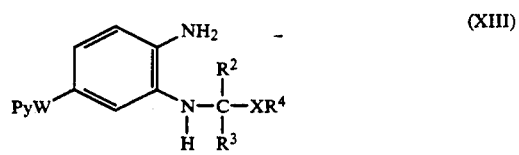
(XIII)

where Py, W, X, $R^2$, $R^3$, $R^4$ are as defined in relation to formula (I) except that in this process W is not NH.

Compounds of formula (XIII) may be produced using methods shown in the following scheme where $R^{24}$ and $R^{25}$ are independently selected from halogen and Py, X, $R^1$, $R^2$, $R^3$ are as defined in relation to formula (I): and W is as defined in relation to formula (I) but is not NH.

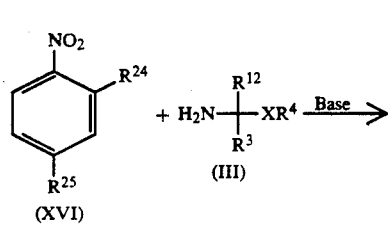
(XVI) (III)

-continued

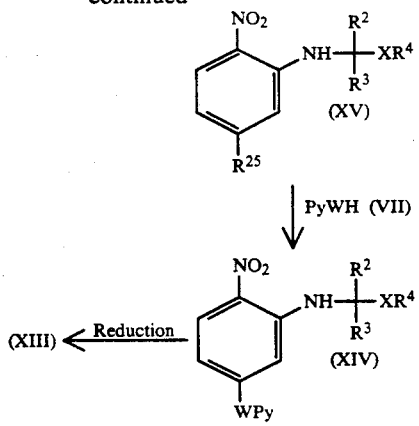

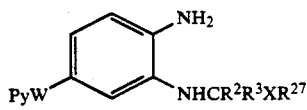

Suitable halide groups $R^{24}$ and $R^{25}$ include chloride and fluoride.

Certain compounds of formula (XIII) are novel and these form a further aspect of the invention. These are compounds of formula (XIIIA):

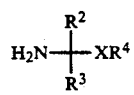

where $R^2$, $R^3$ and X are as defined in relation to formula (I) and $R^{27}$ is a group $R^4$ as defined in relation to formula (I). These compounds can be prepared as described above for the preparation of compounds of formula (XIII).

Reduction of compounds (XIV) may take place using a wide variety of reducing agents selected from the chemical literature by those skilled in the art. The reduction may be carried out for example by using sodium dithionite or tin and hydrochloric acid, iron and hydrochloric acid, or hydrogen or a suitable hydrogen donor such as sodium borohydride with a palladium on charcoal catalyst. The reaction is effected in an organic solvent such as a lower alkyl alcohol optionally mixed with water at temperatures suitably between 20° C. and 90° C.

Reaction of compounds of formula (XV) in which Y is halogen with compounds of formula (VII) may be accomplished using a suitable base. Suitable bases for the reaction include alkali metal hydrides, carbonates and hydroxides or alkoxides. The reaction is preferably carried out in an organic solvent such as dimethylformamide, dimethylsulphoxide, a lower alkanol or a lower ketone. Moderate temperatures for example of from 20° C. to 90° C. are suitably employed. Conveniently the reaction is carried out at 25° C. to 30° C.

Compounds of formula (XV) may be prepared by reaction of dihalonitro compounds (XVI) with suitable compounds of formula (III):

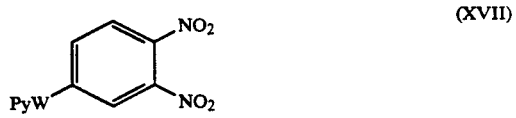

where $R^2$, $R^3$, $R^4$ and X are as defined in relation to formula (I).

This reaction is optionally conducted in the presence of a base. Suitable bases include organic bases such as tertiary amines, e.g. triethylamine, pyridine, dimethylaminopyridine and alkali metal carbonates and alkoxides. The reaction is preferably carried out in an organic solvent such as DMF, DMSO, acetonitrile, tetrahydrofuran or a lower ketone. Moderate temperatures, for example of from 20° C. to 90° C. are suitably employed. Conveniently, the reaction is carried out at 25° C. to 30° C.

Compounds of formula (XVI) are known compounds or they can be prepared from known compounds by known methods as described by Crowther et al (JCS,1949,1260-71); Van Dusen and Schultz (J.Org.Chem, 1956,21,1326-9) and Fisher et al (J.Org.Chem, 1070,35,2240-2).

Compounds of formula (XIV) can be prepared from compounds of formula (XVII):

where Py and W are as defined in relation to formula (XIII) with a compound of formula (XVIII):

where $R^1$, $R^2$, $R^3$, $R^4$ and X are as defined in relation to formula (I) in an organic solvent such as dimethylformamide, dimethylsulphoxide, acetonitrile, tetrahydrofuran or a lower alkyl ketone at moderate temperatures, for example of from 0° C.-90° C. in the presence of a base. Suitable bases include organic bases such as tertiary amines, e.g. triethylamine, pyridine, dimethylaminopyridine and alkali metal carbonates and alkoxides.

Compounds of formula (XVII) are novel and as such form a further aspect of the invention. They may have herbicidal activity in their own right.

Compounds of formula (XVII) can be prepared from compounds of formula (VII) by reaction with 3,4-dinitrofluorobenzene in an organic solvent such as dimethylformamide, dimethylsulphoxide, acetonitrile, tetrahydrofuran or a lower alkyl ketone at moderate temperatures, for example of from 20°-90° C. in the presence of a suitable base. Suitable bases for the reaction include alkali metal hydrides, carbonates, hydroxides or alkoxides.

Compounds of formula (XVIII) are known compounds or may be prepared from known compounds by known methods.

Compounds of formula I where X is $CH_2$ and $R^4$ is CN, CHO or $CO_2R^8$ where $R^8$ is lower alkyl may also be produced by reacting compounds formula (II) as hereinbefore defined with compounds of formula (XIX):

$$R^2 \diagdown \diagup R^{28}$$
$$R^3 \diagup$$
(XIX)

where $R^2$ and $R^3$ are as defined in relation to formula (I) and is CN, CHO or $COOR^{29}$ where $R^{29}$ is lower alkyl in a Michael-type addition in the presence of a base such as Triton B, alkoxides or pyidine at 40° to 100° C. as described by Wiley and Smith (JACS (1954), 76, 4933).

The esters produced may be further modified by standard techniques to give the corresponding acid which may be further modified to give esters, hydrazides, hydraziniums, sulphonamides and other well known acid derivatives.

Compounds (XVII) are known compounds or they can be prepared from known compounds by known methods.

If desired in any of these methods one or more of the following steps may be carried out:
i) when $R^4$ is alkoxycarbonyl hydrolysing to the corresponding acid.
ii) when $R^4$ is COOH esterifying or forming a salt, amide, sulphonamide, hydrazide or hydrazinium derivative.
iii) when $R^4$ is an alcohol, oxidation to the corresponding acid or aldehyde.
iv) when $R^3$ is alkoxycarbonyl, reduction to an alcohol.
v) when $R^4$ is an amide, dehydration to the corresponding nitrile.
vi) when $R^{17}$ is H halogenation to for example Cl or Br.

Steps (i) to (vi) represent standard chemical transformations and reactions. Suitable reactants and reaction conditions will be apparent to the skilled chemist from the literature.

Examples of some of these transformations can be found hereinafter.

The compounds of formula (I) are active as herbicides and therefore, in a further aspect the invention provides a process for severely damaging or killing unwanted plants which process comprises applying to the plants, an effective amount of a compound of formula (I) as hereinbefore defined.

The compounds of formula (I) are active against a broad range of weed species including monocotyledenous and dicotyledonous species. They may show some selectivity towards certain species; they may be used as selective herbicides in rice, soya and wheat crops.

The compounds of formula (I) may be applied directly to the plant (post-emergence application) or to the soil before the emergence of the plant (pre-emergence application). They are particularly useful when applied post-emergence.

The compounds of formula (I) may be used on their own to inhibit the growth of, severely damage, or kill plants but are preferably used in the form of a composition comprising a compound of the invention in admixture with a carrier comprising a solid or liquid diluent.

Therefore, in yet a further aspect, the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; and the lecithins; silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogenous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredients(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and suacorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.01 to 20 kilograms per hectare is suitable while from 0.025 to 10 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having complementary action in the particular application.

Examples of useful complementary herbicides include:

A. benzo-2,1,3-thiadiazin-4-one-2,2-dioxides such as bentazone;
B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (e.g. salts, esters and amides);
C. 1,3 dimethylpyrazole derivatives such as pyrazoxyfen, pyrazolate and benzofenap;
D. Dinitrophenols and their derivatives (e.g. acetates) such as dinoterb, dinoseb and its ester, dinoseb acetate;
E. dinitroaniline herbicides such as dinitramine, trifluralin, ethalflurolin, pendimethalin, oryzalin;
F. arylurea herbicides such as diuron, flumeturon, metoxuron, neburon, isoproturon, chlorotoluron, chloroxuron, linuron, monolinuron, chlorobromuron, daimuron, methabenzthiazuron;
G. phenylcarbamoyloxyphenylcarbamates such as phenmedipham and desmedipham;
H. 2-phenylpyridazin-3-ones such as chloridazon and norflurazon;
I. uracil herbicides such as lenacil, bromacil and terbacil;
J. triazine herbicides such as atrazine, simazine, aziprotryne, cyanazine, prometryn, dimethametryn, simetryne, and terbutryn;
K. phosphorothioate herbicides such as piperophos, bensulide, and butamifos;
L. thiolcarbamate herbicides such as cycloate, vernolate, molinate, thiobencarb, butylate*, EPTC*, triallate, di-allate, esprocarb, tiocarbazil, pyridate, and dimepiperate;
M. 1,2,4-triazin-5-one herbicides such as metamitron and metribuzin;
N. benzoic acid herbicides such as 2,3,6-TBA, dicamba and chloramben;
O. anilide herbicides such as pretilachlor, butachlor, alachlor, propachlor, propanil, metazachlor, metolachlor, acetochlor, and dimethachlor;
P. dihalobenzonitrile herbicides such as dichlobenil, bromoxynil and ioxynil;
Q. haloalkanoic herbicides such as dalapon, TCA and salts thereof;
R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;
S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;
T. cyclohexanedione herbicides such as alloxydim and salts thereof, sethoxydim, cycloxyidim, tralkoxydim, and clethodim;
U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and pyrazosulfuron;
V. imidazolidinone herbicides such as imazaquin, imazamethabenz, imazapyr and isopropylammonium salts thereof, imazethapyr;
W. arylanilide herbicides such as flamprop and esters thereof, benzoylprop-ethyl, diflufenican;
X. amino acid herbicides such as glyphosate and glufosinate and their salts and esters, sulphosate and bialaphos;
Y. organoarsenical herbicides such as monosodium methanearsonate (MSMA);
Z herbicidal amide derivative such as napropamide, propyzamide, carbetamide, tebutam, bromobutide, isoxaben, naproanilide and naptalam;
AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac, dithiopyr and mefanacet;
BB. Examples of useful contact herbicides include: bipyridylium herbicides such as those in which the active entity is paraquat and those in which the active entity is diquat;

* These compounds are preferably employed in combination with a safener such as dichlormid.

The following Examples illustrate the invention:

EXAMPLE 1

This Example illustrates the preparation of compounds 1, 4 and 6:

Step A 5-trifluoromethyl-3-hydroxy-1-methylpyrazole (3.94 g), 5-fluoro-2-nitroaniline (3.7 g) and potassium carbonate (3.27 g) were dissolved in dimethylsulphoxide (30 cm$^3$) and the reaction mixture was stirred at 80° C. for 16 hours. After cooling the mixture was poured into ice/water and the precipitated solid filtered and dried. The yellow solid obtained was triturated with hexane and then dried to afford 5-(1-methyl-5-trifluoromethyl-1H-pyrazol-3-yloxy)-2-nitroaniline (3.68 g) m.p. 91°-2° C.

Step B

The nitroaniline obtained in step A (2 g, 6.6 mmol) was dissolved in 50% aqueous ethanol (100 cm$^3$) and sodium dithionite (4.61 g 26.5 mmol) added portionwise over 20 minutes to the stirred solution, each portion being allowed to dissolve before adding the next. The reaction mixture was heated under reflux with stirring for 1.5 hours and after cooling was poured into water (50 cm$^3$) and neutralised with aqueous sodium bicarbonate before being extracted with ethyl acetate (2×100 cm$^3$). The combined extracts were dried (MgSO$_4$) and the solvent removed in vacuo leaving a light brown solid which was triturated with hexane, filtered and dried, to give 4-(1-methyl-5-trifluoromethyl-1H-pyrazol-3-yloxy)-o-phenylenediamine m.p. 109°-111° C.

Step C

The o-phenylenediamine obtained in step B (1.0 g,3.7 mmol) in water (20 cm$^3$) was treated with concentrated hydrochloric acid (1.7 cm$^3$) at room temperature. After stirring for 15 minutes more water (10 cm$^3$) was added and the mixture cooled in an ice/salt bath to ∼0° C. A solution of sodium nitrite (0.544 g, 7.9 mmol) in water (5.5 cm$^3$) was added dropwise, with stirring, maintaining the temperature at ≦0° C. When the addition was complete the reaction mixture was stirred at 0° C. for 30 minutes and then at room temperature for a further 2 hours. The mixture was extracted several times with ethyl acetate and the combined extracts washed with water, dried (MgSO$_4$) and evaporated leaving 6-(1-methyl-5-trifluoromethyl-1H-pyrazol-3-yloxy)benzotriazole as a buff solid m.p. 129°-131° C.

Step D

The benzotriazole obtained as in step C (3 g,10.6 mmol) was dissolved in acetonitrile (20 cm$^3$) and sulphuryl chloride (1.58 g,11.7 mmol) was added dropwise to the stirred solution with ice-bath cooling so as to maintain the temperature below 25° C. After the addition was complete the mixture was stirred a further 20 minutes before pouring into a solution of sodium bicarbonate (2 g) in water (75 cm$^3$). The aqueous solution was extracted with diethyl ether and the extracts washed with brine and dried (MgSO$_4$) Removal of the solvent gave 6-(4-chloro-1-methyl-5-trifluoromethyl-1H-pyrazol-3-yloxy) benzotriazole as a pale brown solid m.p. 195° C. (dec).

Step E

The benzotriazole obtained in step D (1.59 g 5 mmol) in dimethylformamide (25 cm$^3$) was added dropwise to a stirred suspension of sodium hydride (50% in mineral oil, 120 mg, 5 mmol) and stirring continued for 30 minutes. DL ethyl 2-bromopropionate (0.9 g 5 mmol) in dimethylformamide (25 cm$^3$) was added dropwise and the resultant mixture stirred overnight at room temperature. The reaction mixture was carefully poured into ice/water (100 cm$^3$) and extracted several times with ethyl acetate. The combined extracts were washed with brine and dried (MgSO$_4$) before removing the solvent in vacuo to leave an orange residue. The reaction mixture was further purified by column chromatography on silica gel eluting with hexane/ethyl acetate(2:1) to give fractions containing compound 1, DL ethyl 2-[6-(4-chloro-1-methyl-5-trifluoromethyl-1H-pyrazol -3-yloxy)benzotriazol-2-yl]propionate, and a mixture of the corresponding benzatriazol-1-yl and benzotriazol-3-yl isomers, compounds 6 and 4 respectively.

EXAMPLE 2

This Example illustrates the preparation of compound 7.

Step A

Ethyl DL 2-(5-fluoro-2-nitrophenylamino) propionate (11.35 g, 44 mmol) in acetonitrile (40 cm$^3$) was added to a mixture of 3-hydroxy-1-methyl-5-trifluoromethylpyrazole (7.36 g, 44 mmol) and potassium carbonate (6.07 g, 44 mmol) in acetonitrile (40 cm$^3$). The resulting mixture was heated under reflux for 3 hours, allowed to cool and poured into water. The aqueous mixture was extracted several times with ethyl acetate and the combined extracts dried (MgSO$_4$) before removing the solvent under reduced pressure leaving an orange viscous gum. The product was isolated by column chromatography on silica gel using hexane/ethyl acetate 3:1. DL-ethyl (5-(1-methyl-5-trifluoromethyl-1H-pyrazol-3-yloxy)-2-nitrophenylamino)-2-propionate was obtained as a gum.

Step B

The propionate obtained in step A (5.25 g,13.1 mmol) was dissolved in tetrahydrofuran (25 cm$^3$) and isopropanol (60 ml) added. The solution was treated with a solution of sodium hydroxide (0.576 g,14.4 mmol) in water (6 cm$^3$) and then stirred for 3 hours. The solvent was removed in vacuo leaving sodium DL-(5-(1-methyl-5-trifluoromethyl-1H-pyrazol -3-yloxy-2-nitrophenylamino)-2-propionate as an orange-red residue (5.33 g) which was used without further purification.

Step C

The sodium salt obtained in step B (2.95 g,7.9 mmol) in 2M sodium hydroxide (60 cm$^3$) was added dropwise under nitrogen and during 10 minutes to a suspension of 10% palladium on charcoal (100 mg) and sodium borohydride (726 mg,15.8 mmol) in water (30 cm$^3$). The reaction mixture was stirred at room temperature for 3 hours and filtered through celite affording a light-brown aqueous solution. The filtrate was acidified with 20% hydrochloric acid with cooling to below 0° C. in an ice/salt bath. A solution of sodium nitrite (1.09 g,15.8 mmol) in water (11 cm$^3$) was added dropwise with stirring at such a rate as to maintain the temperature at less than 0° C. On completion of the addition the mixture was allowed to warm to room temperature and extracted several times with ethyl acetate. The combined extracts were dried (MgSO$_4$) and the solvent removed in vacuo to afford a yellow-brown residue.

The residue (1.9 g) was dissolved in dichloroethane (40 cm$^3$), ethanol (270 mg,5.9 mmol) and 4-dimethylaminopyridine (60 mg, 0.5 mmol) were added and the mixture cooled in an ice-bath. Dicyclohexylcarbodiimide (1.1 g, 5.4 mmol) was added portionwise and the mixture stirred overnight at room temperature. A further portion of ethanol (5 cm$^3$) was added and the mixture heated under reflux for 3 hours before being poured into water and extracted with chloroform. The organic extracts were dried (MgSO$_4$) and evaporated leaving a brown residue (2.35 g) which was taken up in hexane/ethyl acetate (2:1) and filtered. The filtrate was evaporated leaving an orange residue (1.21 g) which was purified by column chromatography on silica gel using hexane/ethyl acetate 2:1 as eluant. Compound No. 7, ethyl DL-2-[6-(1-methyl-5-trifluoromethyl-1H-pyrazol-3-yloxy)benzotriazol-1-yl]propionate was obtained as an orange gum (320 mg).

EXAMPLE 3

This Example illustrates the preparation of compound 6.

The pyrazole obtained in Example 2 (400 mg,1.05 mmol) was dissolved in acetonitrile (10 cm$^3$) and sulphuryl chloride (154 mg,0.1 cm$^3$, 1.14 mmol) was added maintaining the temperature below 25° C. After stirring for 1 hour at room temperature the reaction mixture was poured into sodium bicarbonate solution and extracted with ether. The extracts were dried (MgSO$_4$) and evaporated leaving ethyl DL-2-[6-(4-chloro-1-methyl-5-trifluoromethyl-1H-pyrazol-3-yloxy) benzotriazol-1-yl]propionate as an orange-brown viscous gum (350 mg).

EXAMPLE 4

This Example illustrates the preparation of compounds 2, 5 and 7.

The benzotriazole obtained in Step C of Example 1 (2.00 g, 7.1 mmol) in dimethylformamide (30 cm$^3$) was added dropwise to a stirred suspension of sodium hydride (60% in mineral oil, 339 mg, 8.5 mmol) in dimethylformamide (10 cm$^3$) and stirring continued for 5 minutes. DL - ethyl bromopropionate (0.92 cm$^3$, 10.6 mmol) was added dropwise and the mixture stirred at room temperature for 3 hours. The mixture was poured into water (100 cm$^3$) and extracted with diethyl ether (3×100 cm$^3$). The organic extracts were combined, dried (MgSO$_4$), filtered and the filtrate evaporated. The residue was purified by flash column chromatography on silica gel, eluting with diethyl ether/hexane (1:1) to give fractions containing compound 2, DL ethyl 2-[6-(1-methyl-5-trifluoromethyl-1H-pyrazol-3-yloxy) benzotriazol-2-yl]propionate (0.64 g) as a colourless oil, and a mixture of the corresponding benzotriazol-1-yl and benzotriazol-3-yl isomers (1.51 g), compounds 7 and 5 respectively, as an oil.

EXAMPLE 5

This Example illustrates the preparation of compound 3 in Table I.

Compound 2 produced as in Example 4 (0.43 g, 1:1 mmol) was dissolved in a mixture of ethanol (20 cm$^3$) and water (10 cm$^3$), sodium carbonate (0.24 g, 2.2 mmol) was added and the mixture stirred at room temperature for 17 hours. The ethanol was removed under reduced pressure, the aqueous solution acidified with 2N hydrochloric acid and then extracted with ethyl acetate (3×50 cm$^3$). The organic extracts were combined, dried (MgSO$_4$), filtered and the filtrate evaporated to give a colourless oil. Further purification by flash column chromatography on silica gel, eluting with methanol/dichloromethane (1:4) gave Compound 3, DL 2-[6-(4-chloro-1-methyl-5-trifluoromethyl-1H-pyrazol-3-yloxy)benzotriazol-2-yl]propionic acid (0.30 g) as a colourless solid. m.p. 137° C. (dec).

EXAMPLE 6

This Example illustrates the preparation of Compound 9 in Table III.

Step A 4-chloro-3-hydroxy-1-methyl-5-trifluoromethylpyrazole (20.1 g, 0.1 mmol) and potassium carbonate (13.8 g, 0.1 mmol) were stirred in acetonitrile (200 cm$^3$) for ½hour at room temperature. A solution of 3,4-dinitrofluorobenzene (18.6 g, 0.1 mmol) in acetonitrile (100 cm$^3$) was added dropwise, maintaining the internal temperature below 30° C., and the reaction mixture was stirred at room temperature for 19 hours, and then at 70° C. for 4 hours.

The reaction mixture was poured into water (600 cm$^3$) and extracted with ethyl acetate (2×600 cm$^3$). The organic extracts were combined, dried (MgSO$_4$), filtered and concentrated to give a brown solid. Recrystallisation (ethyl acetate/hexane) gave 4-(4-chloro-1-methyl-5-trifluoromethyl-1H -pyrazol-3-yloxy)-o-dinitrobenzene (23.8 g) as a colourless solid m.p. 139°-140° C.

Step B

The dinitrobenzene obtained in Step A (10.0 g, 27.3 mmol) was dissolved in dimethylformamide (40 cm$^3$). Triethylamine (4.6 cm$^3$, 32.7 mmol) and DL 2-aminopropanol (2.6 cm$^3$, 32.7 mmol) were added, and the mixture stirred at room temperature for 17 hours, then at 50° C. for 4 hours. The mixture was cooled to room temperature, poured into diethyl ether (200 cm$^3$) and washed with water (3×200 cm$^3$). The ether layer was collected, dried (MgSO$_4$), filtered and the solvent removed under reduced pressure to give a waxy yellow solid. Recrystallisation (ethyl acetate/hexane) gave DL-2-[5-(4-chloro-1-methyl-5-trifluoromethyl-1H-pyrazol -3-yloxy)-2-nitrophenylamino]-propane-1-ol (8.71 g) as an orange solid. m.p. 118°-120° C.

Step C

The nitrobenzene obtained in Step B (2.55 g, 6.5 mmol) was dissolved in a mixture of tetrahydrofuran (10 cm$^3$) and methanol (20 cm$^3$) and added, dropwise, to a mixture of 10% palladium on charcoal (0.1 g) and sodium borohydride (0.49 g, 12.9 mmol) in water (15 cm$^3$), and the reaction mixture was stirred at room temperature for 1 hour.

The solids were removed by filtration, the filtrate acidified with 2N hydrochloric acid and the solvent removed by evaporation under reduced pressure. The residue was taken up in water (100 cm$^3$) and extracted with ethyl acetate (3×100 cm$^3$). The organic extracts were combined, dried (MgSO$_4$), filtered and the solvent removed under reduced pressure. The residue was further purified by flash column chromatography on silica gel, eluting with ethyl acetate, to give DL-2-[2-amino-5-(4-chloro-1-methyl -5-trifluoromethyl-1H-pyrazol-3-yloxy)phenylamino]propan-1-ol (1.33 g) as an off-white solid m.p. 110°-112° C.

Step D

The diamine obtained in Step C (1.08 g) was dissolved in glacial acetic acid (20 cm$^3$) and water (2 cm$^3$) and cooled to below 5° C. in an ice/salt bath. A solution of sodium nitrite (0.41 g, 5.9 mmol) in water (5 cm$^3$) was added dropwise, at such a rate that the internal temperature was maintained below 5° C., and when the addition was complete the reaction mixture was stirred for 4 hours, during which it was allowed to warm to room temperature. The mixture was poured into ethyl acetate (100 cm$^3$) and washed successively with water (2×100 cm³) and saturated aqueous sodium bicarbonate solution (100 cm³). The organic phase was dried (MgSO₄), filtered and the filtrate evaporated under reduced pressure. The residue was further purified by flash column chromatography on silica gel, eluting with diethyl ether, to give compound 9, DL 2-[6-(4-chloro-1-methyl-5-trifluoromethyl-1H-pyrazol-3-yloxy) benzotriazol-1-yl]-propan-1-ol (0.90 g) as an off white solid m.p. 153°-154° C.

Compound 8 in Table III and compound 17 were prepared by an analogous process using suitable reactants.

EXAMPLE 7

This Example illustrates the preparation of compound 11 in Table III.

Jones reagent was prepared according to Organic Synthesis (1965), 45, 28. Thus, chromium trioxide (6.7 g) was dissolved in water (13 cm³). To this was added concentrated sulphuric acid (5.8 cm³) and the precipitated salts redissolved with water (5 cm³).

A solution of Compound 9 prepared as in Example 6 (0.62 g, 1.7 mmol) was dissolved in acetone (20 cm³) and cooled in an ice/water bath. Jones reagent prepared as above was added in aliquots (0.3 cm³) until 2.1 cm³ had been added. After the final addition the mixture was stirred at room temperature for 17 hours. Isopropanol (5 cm³) was added, and the precipitated salt removed by filtration.

The filtrate was concentrated under reduced pressure, the mixture was taken up in ethyl acetate (100 cm³) and washed with water (3×100 cm³). The organic phase was dried (MgSO₄), filtered and concentrated to give a colourless solid. Trituration with diethyl ether gave Compound 12, DL 2-[6-(4-chloro-1-methyl-5-trifluoromethyl-1H-pyrazol 3-yloxy)benzotriazol-1-yl]-propionic acid (0.36 g) as a colourless solid m.p. 209°-211° C.

Compound 10, 20 and 24 in Table III was prepared by an analgous process using appropriate reactants.

EXAMPLE 8

This Example illustrates the preparation of Compound 6 in Table III.

The acid prepared in Example 7 (0.36 g, 0.9 mmol) was suspended in 1,2-dichloroethane (10 cm³) and cooled in an ice bath. Ethanol (0.5 cm³, excess) and 4-dimethylaminopyridine (0.14 g, 1.1 mmol) were added, followed by dicyclohexylcarbodiimide (0.28 g, 1.4 mmol) and the reaction mixture was stirred for 23 hours. The mixture was filtered, and the filtrate evaporated under reduced pressure. The residue was purified by flash column chromatography, eluting with diethyl ether/hexane (1:1) to give compound 7. DL ethyl 2-[6-(4-chloro-1-methyl -5-trifluoromethyl-1H-pyrazol-3-yloxy)benzotriazol 1-yl]propionate (0.29 g) as a colourless oil.

Compounds 12, 13, 14, 21, 22, 25, 26 and 27 in Table III were prepared by an analogous process using appropriate reactants.

EXAMPLE 9

This Example illustrates the preparation of Compound No. 15 in Table III.

The acid obtained in Example 7 (0.3 g, 0.8 mmol) was suspended in dichloromethane (3 cm³). Oxalyl chloride (168 μl, 1.9 mmol) was added, followed by 1 drop of dimethylformamide, and the reaction mixture stirred at room temperature for 18 hours. The solvent was evaporated under reduced pressure, the residue dissolved in diethyl ether (5 cm³) and methylamine (40% aqueous solution, 1 cm³) added. The mixture was stirred at room temperature for 3 hours, diluted with ethyl acetate (50 cm³) and washed with water (50 cm³). The aqueous phase was extracted with ethyl acetate (2×25 cm³). The organic extracts were combined, dried (MgSO₄), filtered and the filtrate concentrated under reduced pressure. The residue was further purified by flash column chromatography on silica gel, eluting with diethyl ether, to give Compound 15, DL methyl 2-[6-(4-chloro-1-methyl-5-trifluoromethyl-1H-pyrazol-3-yloxy) benzotriazol-1-yl]propionamide (0.21 g) as a colourless solid m.p. 190°-192° C.

Compound 16 in Table III was prepared by an analogous process using appropriate reactants.

EXAMPLE 10

This Example illustrates the preparation of Compound No. 18 in Table III.

DL 2-[6-(4-chloro-1-methyl-5-trifluoromethyl-1-pyrazol -3-yloxy)benzotriazol-1-yl]propionamide (0.18 g, 0.46 mmol) was suspended in a mixture of dichloromethane (10 cm³) and triethylamine (0.13 cm³) and the mixture cooled in a ice-bath. Trichloroacetyl chloride (0.08 cm³, 0.69 mmol) was added and the mixture stirred for 1 hour. The solution was diluted with dichloromethane (10 cm³) and washed with water (20 cm³). The aqueous phase was extracted with dichloromethane and the organic extracts were combined, dried (MgSO₄), filtered and evaporated under reduced pressure. The residue was further purified by flash column chromatography on silica gel, eluting with diethyl ether/hexane (3:1) to give Compound No. 18, DL 2-[6-(4-chloro-1-methyl-5-trifluoromethyl-1H-pyrazol-3-yloxy) -benzotriazol-1-yl]propionitrile (0.07 g) as a colourless solid m.p 147°-150° C.

EXAMPLE 11

This Example illustrates the preparation of Compounds Nos. 19 and 23 in Table III.

Step A 4-(1-methyl-5-trifluoromethyl-1H-pyrazol-3-yloxy)-o-dinitrobenzene (17.7 g, 54.9 mmol) was dissolved in a mixture of glacial acetic acid (90 cm³) and acetic anhydride (10 cm³) and the solution was warmed to 80° C. N-Bromosuccinimide (14.7 g, 82.4 mmol) was added, and the mixture was stirred at 80° C. for 21 hours, and then cooled to room temperature. The precipitate was collected, washed with water, and then taken up in ethyl acetate (500 cm³). The solution was washed with saturated sodium bicarbonate solution (2×300 cm³), dried (MgSO₄), filtered and evaporated under reduced pressure to give 4-(4-bromo-1-methyl-5-trifluoromethyl-1H-pyrazol-3-yloxy)-o-dinitrobenzene (17.5 g) as a colourless solid m.p. 152°-153° C.

Step B

The dinitrobenzene obtained in Step A (10.0 g, 24.3 mmol) was dissolved in N,N-dimethylformamide (60 cm³). Triethylamine (5.1 cm³, 36.5 mmol) and DL 2-aminopropanol 2.9 cm³, 36.5 mmol) were added, and the mixture was stirred at room temperature for 21 hours, and then heated at 70° C. for a further 3 hours. The mixture was cooled to room temperature, poured into diethyl ether (500 cm³) and washed with water (3×300 cm³). The organic layer was dried (MgSO₄), filtered and evaporated under reduced pressure to give DL 2-[5-(4-bromo-1-methyl-5-trifluoromethyl-1H-pyrazol-3-yloxy)-2-nitrophenylamino]propan-1-ol (10.15 g) as an orange solid m.p 116°-118° C.

Step C

The nitrobenzene prepared above (10.15 g, 23.1 mmol) was dissolved in a mixture of tetrahydrofuran (30 cm³) and methanol (60 cm³) and added, dropwise and with external cooling to a mixture of 10% palladium on charcoal (0.75 g) and sodium borohydride (1.76 g, 46.2 mmol) in water (45 cm³), and the reaction mixture was stirred for 30 minutes. The solids were removed by filtration, the filtrate acidified with 2N hydrochloric acid and the solvent removed under reduced pressure. The residue was partitioned between ethyl acetate (400 cm³) and water (400 cm³) and the organic phase dried (MgSO₄), filtered and evaporated under reduced pressure to give a dark brown residue.

The residue obtained above was dissolved in glacial acetic acid (100 cm³) and water (10 cm³) and the mixture was cooled in an ice-bath. A solution of sodium nitrite (3.19 g, 46.2 mmol) in water (10 cm³) was added dropwise, and when the addition was complete the reaction mixture was stirred for 1½ hours. The reaction mixture was diluted with ethyl acetate (300 cm³) and washed successively with water (3×300 cm³) and saturated aqueous sodium bicarbonate solution (300 cm³). The organic phase was dried (MgSO₄), filtered and the filtrate evaporated under reduced pressure. The residue was further purified by flash column chromatography on silica gel, eluting with diethyl ether, and by recrystallisation (ethyl acetate/hexane) to give Compound No. 19, DL 2-[6-(4-bromo-1-methyl-5-trifluoromethyl-1H-pyrazol-3-yloxy)benzotriazol-1-yl]propan-1-ol (4.89 g) as a pale brown solid m.p. 142°-144° C.

Step D

The alcohol obtained in Step C (3.76 g, 8.95 mmol) was dissolved in N,N-dimethylformamide (30 cm³) and imidazole (0.73 g, 10.74 mmol) and tert-butyldimethylsilyl chloride (1.62 g, 10.74 mmol) were added. The reaction mixture was stirred at room temperature for 4 hours and then poured into diethyl ether (150 cm³). The solution was washed with water (3×150 cm³), dried (MgSO₄), filtered and the filtrate evaporated under reduced pressure. The residue was further purified by flash column chromatography on silica gel, eluting with diethylether/hexane (2:3) to give DL 2-[6-(4-bromo-1-methyl-5-trifluoromethyl-1H-pyrazol-3-yloxy) benzotriazol-1-yl]-1-tert-butyldimethylsilyloxypropane (4.27 g) as an off-white solid m.p. 84°-86° C.

Step E

The silylether obtained in Step D (4.12 g, 7.71 mmol) was dissolved in diethylether (80 cm³) and the solution was cooled to below −70° C. under an atmosphere of nitrogen. N-Butyllithium (1.6M solution in hexane, 5 8 cm³, 9.25 mmol) was added, dropwise, and after the addition was complete the reaction mixture was stirred for 15 minutes. Methyl iodide (1.4 cm³, 23.1 mmol) was added, and the reaction mixture was stirred for 1 hour, after which the cooling bath was removed and stirring continued for a further 2 hours. The reaction mixture was poured into water (100 cm³) partitioned and the aqueous phase extracted with diethyl ether (3×50 cm³). The organic extracts were combined, dried (MgSO₄), filtered and the filtrate evaporated under reduced pressure. The residue was taken up in tetrahydrofuran (30 cm³) and tetra n-butylammonium fluoride (1.0M solution in tetrahydrofuran, 10.9 cm³, 10.9 mmol) was added. The reaction mixture was stirred at room temperature for 5 hours. The solvent was evaporated under reduced pressure and the residue partitioned between ethyl acetate (80 cm³) and water (80 cm³). The aqueous phase was extracted with ethyl acetate and the organic extracts were combined, dried (MgSO₄), filtered and the filtrate evaporated under reduced pressure. The residue was purified by flash column chromatography on silica gel, eluting with ethyl acetate/hexane (2:1) to give a colourless solid (2.15 g). Recrystallisation (ethyl acetate/hexane) gave Compound No. 23, DL 2-[6-(1,4-dimethyl-5-trifluoromethyl-1H-pyrazol-3-yloxy]benzotriazol-1-yl]-propan-1-ol as a colourless solid m.p. 114°-117° C.

EXAMPLE 12

This Example illustrates the preparation of Compound No. 28.

Sodium methoxide (0.032 g, 0.60 mmol) was added to a solution of DL 2-[6-(1,4-dimethyl-5-trifluoromethyl-1H-pyrazol-3-yloxy)benzotriazol-1-yl]propionic acid (0.22 g, 0.60 mmol) in methanol (10 cm³) and the reaction mixture was stirred at room temperature for 30 minutes. The solvent was evaporated to afford Compound No. 28. Sodium DL 2-[6-(1,4-dimethyl-5-trifluoromethyl-1H-pyrazol-3-yloxy)benzotriazol-1-yl]propionate (0.22 g) as a colourless solid m.p. 235°-237° C.

Biological Data

The herbicidal activity of the compounds was tested as follows:

Each chemical was formulated by dissolving it in an appropriate amount, dependent on the final spray volume, of a solvent/surfactant blend, which comprised 78.2 gm/liter of Tween 20 and 21.8 gm/liter of Span 80 adjusted to 1 liter using methylcyclohexanone. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to 5 ml with water, glass beads were added and this mixture was then shaken to effect dissolution or suspension of the chemical, after which the beads were removed. In all cases, the mixture was then diluted with water to the required spray volume. If sprayed independently, volumes of 25 cm³ and 30 cm³ were required for pre-emergence and post-emergence tests respectively; if sprayed together, 45 cm³ was required. The sprayed aqueous emulsion contained 4% of the initial solvent/surfactant mix and the test chemical at an appropriate concentration.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 9 where 0 is 0% damage, 1 is 1-5% damage, 2 is 6-15% damage, 3 is 16-25% damage, 4 is 26-35% damage, 5 is 36-59% damage, 6 is 60-69% damage, 7 is 70-79% damage, 8 is 80-89% damage and 9 is 90-100% damage.

In a test carried out to detect pre-emergence herbicidal activity, crop seeds were sown at 2 cm depth (i.e.

Sb, Ct, Rp, Ww, Mz, Rc, Sy) and weed seeds at 1 cm depth beneath compost and sprayed with the compositions at the rate of 1000 liters per hectare. 20 days after spraying, the seedlings in the sprayed plastic trays were compared with the seedlings in unsprayed control trays, the damage being assessed on the same scale of 0 to 9.

The results of the tests are given in Table IV below.

TABLE IV

| COMPOUND NO. | APPLICATION | PRE- OR POST-EMERGENCE APPLICATION | TEST PLANTS (see Table V) | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | | Sb | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
| 1 | Pre | 1 | 3 | 0 | 5 | 0 | 0 | 0 | 0 | | 9 | | 0 | 0 | 5 | 9 | 0 | 0 | | 0 | 0 | | 0 | 6 | 0 | 0 | 4 | |
| | Post | | 9 | 5 | 2 | 9 | 7 | 1 | 0 | 8 | 9 | 8 | 9 | 2 | 9 | 9 | 2 | 0 | 9 | 0 | 0 | 2 | 5 | 0 | 1 | 4 | 0 |
| 2 | Pre | 1 | 0 | 3 | 2 | 0 | 0 | 0 | 0 | 0 | 0 | | 0 | 2 | 0 | 0 | 3 | 0 | 2 | 0 | 0 | 0 | 0 | 0 | 6 | 0 | 0 |
| | Post | | 7 | 5 | 4 | 2 | 7 | 0 | 0 | 1 | 9 | | 0 | 2 | 1 | 0 | 7 | 0 | 9 | 0 | 2 | 0 | 2 | 0 | 2 | 0 | 0 |
| 3 | Pre | 1 | 2 | 0 | 0 | 2 | 0 | 0 | 0 | 0 | 2 | | 0 | 0 | 0 | 4 | 0 | 3 | | 0 | 0 | 0 | 0 | 0 | 6 | 0 | 0 |
| | Post | | 3 | 0 | 6 | 5 | 0 | 0 | 0 | 4 | 9 | 5 | 9 | 2 | 4 | 9 | 3 | 0 | 9 | 0 | 0 | 0 | 4 | 9 | 0 | 5 | 0 |
| 6 | Pre | 1 | 8 | 3 | 3 | 0 | 9 | 0 | 0 | 9 | 9 | 9 | 9 | 2 | 9 | 9 | 2 | 2 | 9 | 3 | 0 | 2 | 9 | 2 | 8 | 9 | 9 | 6 |
| | Post | | 9 | 2 | 0 | 9 | 5 | 7 | 4 | 9 | 9 | 8 | 9 | 9 | 3 | 9 | 9 | 1 | 1 | 9 | 6 | 0 | 5 | 5 | 7 | 4 | 7 | 5 |
| 7 | Pre | 1 | 9 | 0 | 9 | 0 | 0 | 5 | 3 | 9 | 4 | 8 | 9 | 0 | 3 | 7 | 3 | 2 | 9 | 0 | 0 | 2 | 5 | 7 | 4 | 3 | 3 | 9 |
| | Post | | 0 | 8 | 0 | 9 | 5 | 1 | 0 | 9 | 9 | 9 | 9 | 6 | 9 | 9 | 9 | 9 | 2 | 9 | 2 | 2 | 5 | 0 | 7 | 5 | 9 | 9 |
| Mixture of 6 and 4 | Pre | 2 | 6 | 0 | 0 | 2 | 0 | 6 | 0 | 0 | 9 | 8 | 9 | 0 | 0 | 3 | 7 | 3 | | | 0 | 0 | 2 | 0 | 9 | 9 | 3 | 9 |
| | Post | | 9 | 9 | 9 | 9 | 9 | 6 | 5 | 9 | 9 | 9 | 9 | 9 | 9 | 9 | 9 | 9 | | 9 | 2 | 3 | 5 | 9 | 9 | 9 | 9 | 9 |

(Table continues with compounds 8 through 27 at various application rates: 0.25, 0.0625, 0.15, 0.025, 0.0615, 1)

TABLE V

| Test Plants |
|---|
| Sb - Sugar beet |
| Rp - Rape |
| Ct - Cotton |
| Sy - Soybean |
| Mz - Maize |
| Ww - Winter wheat |
| Rc - Rice |
| Bd - *Bidens pilosa* |
| Ip - *Ipomoea lacunosa* (pre-emergence) |
|    *Ipomoea hederacea* (post-emergence) |
| Am - *Amaranthus retroflexus* |
| Pi - *Polygonum aviculare* |
| Ca - *Chenopodium album* |
| Ga - *Galium aparine* |
| Xa - *Xanthium spinosum* |
| Xs - *Xanthium strumarium* |
| Ab - *Abutilon theophrasti* |
| Eh - *Euphorbia heterophylla* |
| Av - *Avena fatua* |
| Dg - *Digitaria sanguinalis* |
| Al - *Alopecurus myosuroides* |
| St - *Setaria viridis* |
| Ec - *Echinochloa crus-galli* |
| Sh - *Sorghum halepense* |
| Ag - *Agropyron repens* |
| Ce - *Cyperus esculentes* |

We claim:

1. A compound of formula (I):

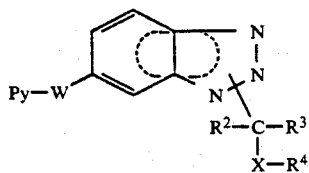

in which
the dotted line indicates the presence of two double bonds arranged so as to form a fused hetero aromatic ring system;
Py is an optionally substituted pyrazole ring;
W is O or $NR^1$; where $R^1$ is hydrogen or $C_1-C_3$ alkyl;
X is $(CH_2)_n$, $CH=CH$, $CH(OR^5)CH_2$, or $COCH_2$; where n is 0, 1 or 2;
$R^2$ and $R^3$ are independently selected from H, optionally substituted $C_1-C_{10}$ alkyl, $C_2-C_{10}$ alkenyl or $C_3-C_{10}$ alkynyl, halogen, or $NR^6R$, and $R^2$ and $R^3$ together with the carbon to which they are attached form an optionally substituted $C_2-C_{10}$ alkenyl group or a $C_3-C_9$ cycloalkyl group;
$R^4$ is $CO_2R^8$, CN, $COR^8$, $CH_2OR^8$, $CH(OH)R^8$, $CH(OR^8)R^9$, $CSNH_2$, $COSR^8$, $CSOR^8$, $CONHSO_2R^8$, $CONR^{10}R^{11}$, $CONHNR^{10}R^{11}$, $CONHN^+R^{10}R^{11}R^{12}R^{14-}$, $CO_2^-R^{15+}$ or $COON=CR^{10}R^{11}$;
$R^{15+}$ is an agriculturally acceptable cation and $R^{14-}$ is an agriculturally acceptable anion;
$R^5$, $R^8$ and $R^9$ are independently selected from H or an optionally substituted $C_1-C_{10}$ alkyl, phenyl, $C_2-C_{10}$ alkenyl or $C_2-C_{10}$ alkynyl group;
$R^6$, $R^7$, $R^{10}$, $R^{11}$ and $R^{12}$ are independently selected from H or an optionally substituted $C_1-C_{10}$ alkyl, $C_2-C_{10}$ alkenyl, phenyl or $C_2-C_{10}$ alkynyl group; or any two of $R^6$, $R^7$, $R^{10}$, $R^{11}$ and $R^{12}$ together with the atom to which they are attached form a $C_3-C_9$ cycloalkyl, pyrrolidine, piperidine or morpholine ring;
and wherein:

(i) optional substituents for the pyrazole ring comprise up to 3 members selected from halogen; a group $R^x$ where $R^x$ is a group as defined hereinbefore for $R^8$; nitro, $C_1-C_{10}$ haloalkoxy; a group $S(O)_mR^y$ where m is 0, 1 or 2 and $R^y$ is a group as hereinbefore defined for $R^8$; or $R^z$ where $R^z$ is a group as hereinbefore defined for $R^4$;

(ii) optional substituents for phenyl groups $R^5$, $R^6$, $R^7$, $R^8$, $R^9$, $R^{10}$, $R^{11}$, $R^{12}$ and $R^{13}$ comprise up to 5 members selected from halogen, $C_1-C_3$ alkyl, $C_1-C_{10}$ haloalkyl, $C_1-C_{10}$ haloalkoxy, nitro, cyano, $C_1-C_3$ alkoxy or $S(O)_qR^w$ where q is 0, 1 or 2 and $R^w$ is $C_1-C_{10}$ alkyl; and (iii) optional substituents for alkyl, alkenyl and alkynyl groups $R^2$, $R^3$, $R^4$, $R^5$, $R^6$, $R^7$, $R^8$, $R^9$, $R^{10}$, $R^{11}$ and $R^{12}$ comprise one or more members selected from halogen; nitro; cyano; phenyl; $CO_2R^{19}$, $NHCOR^{19}$ or $NHCH_2CO_2R^{19}$ where $R^{19}$ is hydrogen, $C_1-C_6$ alkyl or an agriculturally acceptable cation; $C_1-C_6$ alkoxy; oxo; $S(O)_qR^w$ where q is 0, 1 or 2 and $R^w$ is $C_1-C_{10}$ alkyl; amino; mono- or di- ($C_1-C_6$ alkyl)amino; $CONR^{20}R^{21}$ where $R^{20}$ and $R^{21}$ are independently selected from hydrogen; $C_1-C_6$ alkyl, $C_2-C_6$ alkenyl or $C_2-C_6$ alkynyl, or $R^{20}$ and $R^{21}$ together form a tetrahydrofuranyl ring.

2. A compound according to claim 1 wherein Py is a group of sub-formula:

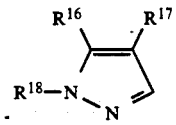

wherein
$R^{16}$ is halogen, CN, $C_1-C_{10}$ haloalkyl, optionally substituted $C_1-C_{10}$ alkyl, $S(O)_mR^y$; where m is 0, 1 or 2, and $R^y$ is a group as defined in claim 1 for $R^8$;
$R^{17}$ is H, halogen, CN, $C_1-C_{10}$ alkyl, $C_1-C_{10}$ haloalkyl, nitro, $S(O)_mR^y$ where m and $R^y$ are as hereinbefore defined or a group $R^z$ where $R^z$ is a group as defined in claim 1 for $R^4$; and
$R^{18}$ is optionally substituted $C_1-C_{10}$ alkyl, $C_2-C_{10}$ alkenyl or $C_2-C_{10}$ alkynyl.

3. A compound according to claim 2 where $R^{16}$ is haloalkyl.

4. A compound according to claim 2 where $R^{17}$ is hydrogen, halogen or methyl.

5. A compound according to claim 2 where is $C_{1-6}$ alkyl.

6. A compound according to claim 1 wherein $R^4$ is selected from a group $CO_2R^8$, CN, $CH_2OR^8$, $CONR^{10}R^{11}$, $COON=CR^{10}R^{11}$ or $CONHN^+R^{10}R^{11}R^{12}R^{14-}$, where $R^8$, $R^{10}$, $R^{11}$, $R^{12}$ and $R^{14-}$ are as defined in claim 1.

7. A compound according to claim 6 where $R^4$ is a group $CO_2R^8$ where $R^8$ is $C_{1-6}$ alkyl.

8. A compound according to claim 1 where X is $(CH_2)_n$ where n is 0 or 1.

9. A compound according to claim 1 where W is oxygen.

10. A method of killing or controlling the growth of unwanted plants which method comprises applying to the plants or to a locus thereof an effective amount of a compound of formula (I) as defined in claim 1.

11. A herbicidal composition comprising a herbicidally effective amount of a compound as defined in claim 1 in combination with a carrier.

* * * * *